US010617844B2

(12) United States Patent
McNabb et al.

(10) Patent No.: US 10,617,844 B2
(45) Date of Patent: Apr. 14, 2020

(54) MEDICAL DEVICE PACKAGE

(71) Applicant: Covidien LP, Mansfield, MA (US)

(72) Inventors: Thomas McNabb, Alta Loma, CA (US); John Muri, Laguna Niguel, CA (US)

(73) Assignee: Covidien LP, Mansfield, MA (US)

( * ) Notice: Subject to any disclaimer, the term of this patent is extended or adjusted under 35 U.S.C. 154(b) by 369 days.

(21) Appl. No.: 15/451,050

(22) Filed: Mar. 6, 2017

(65) Prior Publication Data

US 2018/0250495 A1    Sep. 6, 2018

(51) Int. Cl.
*B65D 85/04*   (2006.01)
*A61M 25/00*   (2006.01)
*B65D 77/00*   (2006.01)

(52) U.S. Cl.
CPC ......... *A61M 25/002* (2013.01); *B65D 77/003* (2013.01); *B65D 85/04* (2013.01)

(58) Field of Classification Search
CPC ...... A61M 25/002; A61B 50/30; A61B 50/33; A61B 2050/3007; B65D 85/04; B65D 77/003
USPC ......................................... 206/363, 364, 438
See application file for complete search history.

(56) References Cited

U.S. PATENT DOCUMENTS

| | | | |
|---|---|---|---|
| 3,514,171 A | 5/1970 | McGaha | |
| 4,688,674 A | 8/1987 | Stirtz | |
| 4,721,123 A * | 1/1988 | Cosentino | A61M 25/002 134/113 |
| 4,886,500 A | 12/1989 | Lazarus | |
| 5,098,391 A | 3/1992 | Pantages et al. | |
| 5,526,928 A | 6/1996 | Yabe et al. | |
| 5,575,382 A * | 11/1996 | Sobel | A61B 17/06123 206/380 |
| 5,738,213 A * | 4/1998 | Whiting | A61M 25/002 206/210 |
| 5,769,222 A | 6/1998 | Banerian | |
| 6,068,121 A * | 5/2000 | McGlinch | A61M 25/002 206/364 |
| 6,533,116 B1 * | 3/2003 | Riley | A61M 25/002 206/363 |
| 6,691,946 B2 * | 2/2004 | Dannecker | A61M 25/002 242/400.1 |
| 7,334,678 B2 | 2/2008 | Kesler et al. | |
| 7,766,162 B2 * | 8/2010 | Maki | A61M 25/002 206/364 |

(Continued)

OTHER PUBLICATIONS

U.S. Appl. No. 15/431,339, filed Feb. 13, 2017, by Christopher Anderson.

(Continued)

*Primary Examiner* — Steven A. Reynolds
(74) *Attorney, Agent, or Firm* — Shumaker & Sieffert P.A.

(57) ABSTRACT

In some examples, a medical device package may include a tray and a lip. The tray defines a recess configured to receive an elongated medical device in a coiled state. The lip is configured to cover at least a portion of the recess. The lip and tray define a mouth to the recess. The tray and lip define an opening configured to expose the elongated medical device when the elongated medical device is received in the recess. The mouth is configured to facilitate removal of the elongated medical device from the recess through the opening while the elongated medical device is in the coiled state.

25 Claims, 10 Drawing Sheets

(56) References Cited

U.S. PATENT DOCUMENTS

| | | | |
|---|---|---|---|
| 8,020,703 B2 | 9/2011 | List et al. | |
| 8,239,040 B2 | 8/2012 | Geistert | |
| 8,439,193 B2 * | 5/2013 | Koellhofer | A61M 25/002 134/117 |
| 8,662,306 B2 * | 3/2014 | Agrawal | A61M 25/002 206/370 |
| 8,702,619 B2 | 4/2014 | Wang | |
| 9,687,300 B2 * | 6/2017 | Hartfelder | B65B 69/00 |
| 2002/0157981 A1 | 10/2002 | Whiting et al. | |
| 2008/0023346 A1 * | 1/2008 | Vonderwalde | A61F 2/0095 206/210 |
| 2014/0110296 A1 * | 4/2014 | Terzibashian | A61M 25/002 206/438 |
| 2016/0206394 A1 | 7/2016 | Lampropoulos et al. | |

OTHER PUBLICATIONS

International Search Report and Written Opinion of International Application No. PCT/US2018/020425, dated Jul. 10, 2018, 13 pp.
International Preliminary Report on Patentability issued in counterpart International Application No. PCT/US2018/020425, dated Sep. 10, 2019, 9 pp.
Communication Pursuant to Rules 161(1) and 162 EPC dated Oct. 15, 2019 from counterpart European Application No. 18723999.1, 3 pp.

* cited by examiner

MEDICAL DEVICE PACKAGE

TECHNICAL FIELD

This disclosure relates to packages for medical devices.

BACKGROUND

Elongated medical devices, such as catheters, may be packaged in a relatively compact configuration prior to use. For example, a catheter may be stored in a sheath that is clipped together into a coiled arrangement for shipment and storage prior to use by a clinician during a medical procedure.

SUMMARY

This disclosure describes example medical device packages that are configured to receive and house elongated medical devices in coiled states, and facilitate the removal of elongated medical devices from the package in the respective coiled states. In some examples, a medical device package may include a tray and a lip. The tray may define a recess that is configured to receive the elongated medical device in the coiled state. The lip may cover a portion of the recess, and due to a relative arrangement of the tray and lip, a mouth is defined between the lip and tray that exposes an elongated medical device disposed within the recess. The lip and tray together may define an opening through which the elongated medical device may be accessed. The mouth may be configured to facilitate removing the elongated medical device through the opening while the elongated medical device is still in the coiled state.

Clause 1: In one example, a medical device package includes a tray defining a recess configured to receive an elongated medical device in a coiled state and a lip configured to cover at least a portion of the recess, the lip and tray defining a mouth to the recess, wherein the tray and lip define an opening configured to expose the elongated medical device when the elongated medical device is received in the recess, the mouth being configured to facilitate removal of the elongated medical device from the recess through the opening while the elongated medical device is in the coiled state.

Clause 2: In some examples of the medical device package of clause 1, the tray defines a generally flat major surface, wherein the elongated medical device rests on the major surface when the elongated medical device is received in the recess.

Clause 3: In some examples of the medical device package of any of clauses 1-2, the major surface is generally continuous within the recess.

Clause 4: In some examples of the medical device package of any of clauses 1-3, the recess extends around an entirety of a perimeter of the tray.

Clause 5: In some examples of the medical device package of any of clauses 1-4, the opening fluidically exposes an entirety of the elongated medical device when the elongated medical device is received by the recess.

Clause 6: In some examples of the medical device package of any of clauses 1-5, the recess is configured such that the elongated medical device contacts a surface of the tray that runs along a perimeter of the tray and is generally opposite the mouth when the recess receives the elongated medical device in the coiled state.

Clause 7: In some examples of the medical device package of any of clauses 1-6, the lip recedes to a perimeter of the tray.

Clause 8: In some examples of the medical device package of any of clauses 1-7, an inner edge of the lip has a radius than is greater than a radius of an outer edge of the lip minus a radial distance between the outer edge and the inner edge such that the lip curls away from the tray as the lip radially extends toward a center of the tray.

Clause 9: In some examples of the medical device package of any of clauses 1-7, the inner edge of the lip has a radius that is smaller than a radius of an outer edge of the lip minus a radial distance between the outer edge and the inner edge such that the lip curls towards the tray as the lip radially extends toward a center of the tray.

Clause 10: In some examples of the medical device package of any of clauses 1-9, the lip is flexible such that the lip is configured to flex in response to a force of the elongated medical device being pulled laterally from the medical device package in the coiled state.

Clause 11: In some examples of the medical device package of any of clauses 1-10, the lip is configured to be received by the tray.

Clause 12: In some examples of the medical device package of any of clauses 1-11, the tray defines an indentation configured to retain at least a portion of the elongated medical device.

Clause 13: In some examples of the medical device package of clause 12, the indentation is configured to retain the portion of the elongated medical device at a location physically separate from the recess.

Clause 14: In some examples of the medical device package of clause 12, the portion of the elongated medical device comprises at least one of a stent location or a hub of the elongated medical device.

Clause 15: In some examples of the medical device package of any of clauses 1-14, the tray defines a profile configured to mate with another medical device package.

Clause 16: In some examples of the medical device package of any of clauses 1-15, the tray defines a drain hole configured to drain fluid from the recess.

Clause 17: In some examples of the medical device package of any of clauses 1-16, the coiled state includes a plurality of loops of the elongated medical device.

Clause 18: In some examples of the medical device package of any of clauses 1-17, the tray defines a generally circular planform through the recess.

Clause 19: In some examples of the medical device package of any of clauses 1-17, the tray defines a generally ovaloid planform through the recess.

Clause 20: In some examples of the medical device package of any of clauses 1-19, the tray further comprises one or more strengthening ribs.

Clause 21: In some examples of the medical device package of clause 20, the one or more strengthening ribs are located on a surface opposite the opening.

Clause 22: In some examples of the medical device package of any of clauses 1-21, the medical device package further comprises a pouch, wherein the tray and lip are configured to fit within the pouch.

Clause 23: In some examples of the medical device package of any of clauses 1-22, the tray is constructed of a material that is configured to withstand a sterilization temperature of about 50° C.

Clause 24: In some examples of the medical device package of any of clauses 1-23, the medical device package further comprises the elongated medical device within the recess of the tray.

Clause 25: In some examples of the medical device package of any of clauses 1-10 or 12-24, the tray and lip are a unitary structure.

Clause 26: In some examples of the medical device package of any of clauses 1-25, the recess as defined by the tray is continuous with a circular planform.

Clause 27: In some examples of the medical device package of any of clauses 1-26, the tray further comprises a surface configured to be written on.

Clause 28: In some examples of the medical device package of any of clauses 1-27, the tray includes a retention member configured to retain a medical component that is structurally separate from the elongated medical device.

Clause 29: In one example, a medical device package includes a tray defining a recess configured to receive an elongated medical device in a coiled state and the elongated medical device within the recess in the coiled state and a lip configured to cover a portion of the recess and retain the elongated medical device within the portion of the recess, wherein the lip and tray define a mouth configured to provide access to the portion of the recess, wherein the tray and lip define an opening configured to expose the elongated medical device when the elongated medical device is received in the recess, the mouth being configured to facilitate removal of the elongated medical device in a lateral direction from the recess through the opening while the elongated medical device is in the coiled state.

Clause 30: In some examples of the medical device package of clause 29, the elongated medical device is retained by an inner edge of the lip that has a radius than is greater than a radius of an outer edge of the lip minus a radial distance between the outer edge and the inner edge such that the lip curls away from the tray as the lip radially extends toward a center of the tray.

Clause 31: In some examples of the medical device package of any of clauses 29-30, the tray defines an indentation configured to retain at least a portion of the elongated medical device.

Clause 32: In some examples of the medical device package of clause 31, the indentation is configured to retain the portion of the elongated medical device at a location physically separate from the recess.

Clause 33: In some examples of the medical device package of clause 31, the indentation is configured to retain the portion of the elongated medical device at a location that is visually separate from the recess.

Clause 34: In some examples of the medical device package of clause 31, the indentation is retaining at least one of a stent location or a hub of the elongated medical device.

Clause 35: In one example, a medical device package includes a tray defining a major surface and a first wall that extends out from the major surface along a perimeter of the major surface, the major surface and the first wall defining a recess configured to receive an elongated medical device in a coiled state and a lip connected to the first wall and extending around a portion of the perimeter of the major surface, the lip being configured to cover a part of the recess, and the lip and the major surface of the tray defining a mouth to the recess, wherein the lip and tray define an opening configured to expose the recess, the mouth being configured to facilitate removal of the elongated medical device from the part of the recess while the elongated medical device is in the coiled state, wherein the medical device package is configured to facilitate the removal of the elongated medical device in a radial direction away from the portion of the perimeter.

Clause 36: In one example, a method of facilitating the hydration and removal of an elongated medical device in a medical device package in a coiled state includes forming the medical device package with a tray defining a recess configured to receive the elongated medical device in the coiled state and a lip configured to cover a portion of the recess, the lip and tray defining a mouth to the recess, wherein the tray and lip define an opening configured to expose the elongated medical device when the elongated medical device is received in the recess, the mouth being configured to facilitate the removal of the elongated medical device through the opening while the elongated medical device is in the coiled state in a lateral direction relative to the longitudinal axis of the elongated medical device, wherein the opening is configured to fluidically expose the entirety of the elongated medical device such that the entirety of the elongated medical device is contacted by hydrating fluid when the medical device package is at least partially submerged in a container of hydrating fluid.

Clause 37: In some examples of the method of clause 36, the method further comprises forming a plurality of medical device packages that are each substantially similar to the medical device package and facilitating the hydration of a plurality of elongated medical devices housed in the plurality of medical device packages by configuring the plurality of medical device packages to all fit within the container of hydrating fluid.

Clause 38: In some examples of the method of any of clauses 36-37, each medical device package of the plurality of medical device packages is configured to stack and interlock with other medical device packages of the plurality of medical device packages within the container of hydrating fluid while maintaining fluidical exposure of each elongated medical device of each respective medical device package.

Clause 39: In some examples of the method of any of clauses 36-38, the method further comprises placing the tray that has received the lip and elongated medical device in a pouch.

Clause 40: In some examples of the method of any of clauses 36-39, the method further comprises sealing the pouch with the tray that has received the lip and elongated medical device within the pouch.

Clause 41: In some examples of the method of any of clauses 36-40, the method further comprises sterilizing the elongated medical device within the pouch.

Clause 42: In one example, a medical device package includes a package body having a channel configured to receive an elongated medical device in a coiled configuration and the channel having a mouth that faces toward a central region of the package body to define a removal path of the elongated medical device that extends laterally from the channel toward the central region.

Clause 43: In some examples of the medical device package of clause 42, the channel mouth permits the elongated medical device to be removed from the channel while the elongated medical device is in the coiled configuration.

Clause 44: In some examples of the medical device package of any of clauses 42-43, the channel is located in a periphery of the package body.

Clause 45: In some examples of the medical device package of clause 44, the mouth extends along an inner edge of the channel.

Clause 46: In some examples of the medical device package of clause 45, the mouth extends continuously around 180 degrees or more of a circumference of the central region.

Clause 47: In some examples of the medical device package of any of clauses 42-46, the channel comprises a first wall located outward of the mouth and facing inward toward the central region.

Clause 48: In some examples of the medical device package of clause 47, the elongated medical device tends to uncoil in the absence of restraint, such that at least a portion of the elongated medical device abuts and is restrained by the first wall.

Clause 49: In some examples of the medical device package of clause 47, the first wall maintains the elongated medical device in the coiled configuration.

Clause 50: In some examples of the medical device package of any of clauses 42-49, the central region of the package body comprises a physical surface of the body.

Clause 51: In some examples of the medical device package of any of clauses 42-50, the central region of the package body comprises a void.

Clause 52: In some examples of the medical device package of any of clauses 42-51, the channel has a circular, oval or D-shaped planform.

Clause 53: In some examples of the medical device package of any of clauses 42-52, the channel extends along a first portion of the periphery of the package body, but not along a second portion of the periphery.

Clause 54: In some examples of the medical device package of clause 53, the second portion of the periphery comprises an exit ramp that extends upward and outward away from the central region.

Clause 55: In some examples of the medical device package of any of clauses 42-54, the channel forms first and second ends that are spaced apart by an open region that exposes a portion of the coiled elongated medical device for manual grasping and separation from the package body.

Clause 56: In some examples of the medical device package of clause 55, the channel forms a partial loop in planform and the first and second ends form ends of the partial loop.

Clause 57: In some examples of the medical device package of any of clauses 56, the partial loop has a greater length along the periphery of the package body than does the open region.

Clause 58: In some examples of the medical device package of clause 56, wherein the open region forms an exit ramp that extends upward and outward away from the central region.

Clause 59: In some examples of the medical device package of any of clauses 42-58, the package body comprises a tray.

Clause 60: In some examples of the medical device package of clause 59, the package body further comprises a lip, and the lip forms a portion of the channel.

Clause 61: In some examples of the medical device package of any of clauses 42-60, the package body comprises a hoop.

Clause 62: In some examples of the medical device package of any of clauses 42-61, the package body has an overall planar or plate-like configuration.

Clause 63: In some examples of the medical device package of any of clauses 42-62, the package body forms an opening configured to expose the elongated medical device when the elongated medical device is received in the channel.

Clause 64: In one example, a method of hydrating an elongated medical device received in the channel of the medical device package of any of clauses 43-63 includes submerging the package and elongated medical device in a hydration liquid so that the hydration liquid passes through the mouth into the channel to come into contact with the elongated medical device.

Clause 65: In one example, a method of removing an elongated medical device received in the channel of the medical device package of any of clauses 43-63 includes moving the elongated medical device out of the channel through the mouth without uncoiling the medical device before moving it through the mouth.

Clause 66: In some examples of the medical device package of any of clauses 42-63, the channel forms one or more gaps therein.

Clause 67: In some examples of the medical device package of any of clauses 42-63, the gaps expose the elongated medical device when it is received in the channel.

Clause 68: In some examples of the medical device package of any of clauses 42-63, the gaps are formed in a wall of the channel.

The details of one or more examples are set forth in the accompanying drawings and the description below. Other features, objects, and advantages will be apparent from the description and drawings, and from the claims.

DETAILED DESCRIPTION

Figure 1:
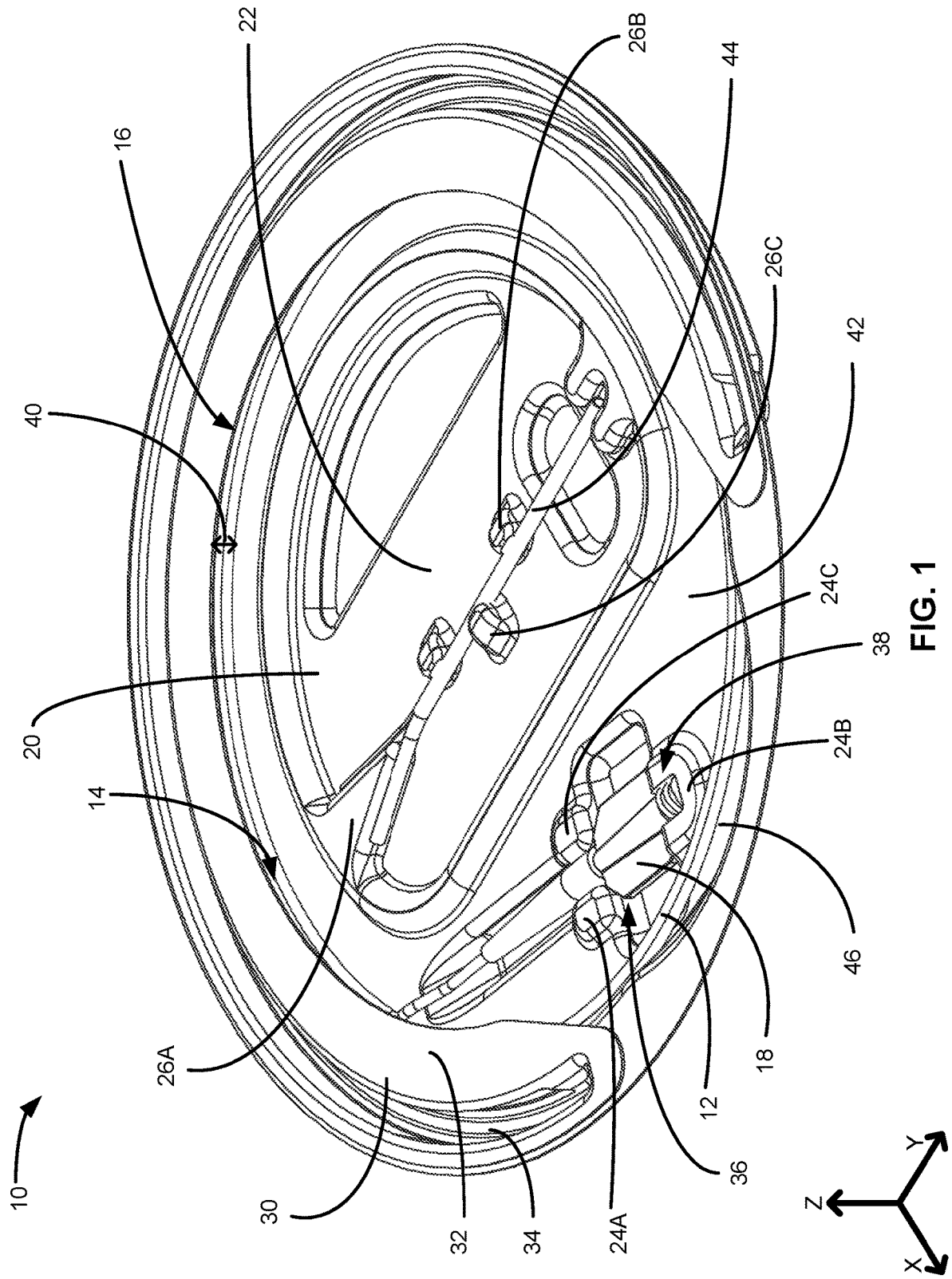
FIG. 1 depicts a perspective view of an example medical device package, in which an example elongated medical device and an example medical component are packaged.

Elongated medical devices, such as catheters, may be packaged for shipment and storage after manufacture and before being used in a medical procedure. An elongated medical device may be packaged in a configuration other than a linear configuration (e.g., where the device may be held in a straight configuration) in order to provide for more efficient storage of the elongated medical device (e.g., by storing the medical device in a package having a footprint with at least one smaller dimension than the linear configuration of the medical device). For example, the medical device may be stored in a package having a smaller length than the total length of the medical device, measured along a longitudinal axis of the medical device. In addition, storing the elongated medical device in a non-linear configuration may help reduce shipping costs, provide for easier/less awkward manipulation of the medical device package, or any combination thereof.

The medical device package may also help isolate the elongated medical device from the surrounding environment, help protect the structural integrity of the medical device, help prevent contamination of the elongated medical device during shipping and/or storage, or both help protect the structural integrity of the medical device and help prevent contamination of the medical device.

Some medical device packages may comprise an outer sheath (e.g., relatively rigid polymeric tubing) that receives the elongated medical device. The sheath of the medical device packaging may be clipped to itself or otherwise fused/held together in a coiled shape, such that the elongated medical device is received within the sheath while the sheath is in the coiled shape. Such a medical device packaging sheath may be referred to as a "snail pack." A clinician may remove the elongated medical device from the snail pack by longitudinally pulling the elongated medical device out of one end of the sheath of the snail pack (e.g., pulling the elongated medical device along a longitudinal axis of the elongated medical device). Some elongated medical devices may be upwards of 2.5 meters long, making the removal of the elongated medical device from the sheath by pulling along the length of the elongated medical device a cumbersome and unwieldy task.

After removing the elongated medical device from the coiled sheath of the snail pack, the clinician may "re-coil" the elongated medical device, e.g., to facilitate hydration of the medical device in a bowl or other container of hydration liquid such as saline solution, or to otherwise facilitate use of the medical device. The removal of an elongated medical device from a coiled sheath and the subsequent re-coiling of the elongated medical device may be time consuming, particularly when multiple elongated medical devices stored in similar medical device snail packs are used for a single medical procedure.

In some cases, the medical device package may affect the performance or production yield of the elongated medical device. For example, loading an elongated medical device into a sheath of a snail pack or another outer sheath of a medical device package by pushing the elongated medical device into the sheath along the longitudinal axis of the elongated medical device may add stress to the elongated medical device. The added stress may adversely affect the defect rate associated with the packaging process. As another example, the elongated medical device may kink during the removal of the elongated medical device from the sheath of the snail pack or during the insertion of the medical device into the snail pack, and the kinking may adversely affect the performance of the medical device in a medical procedure. For example, the kinking may adversely affect the navigability of the elongated medical device through vasculature of a patient.

In addition, in some cases, removing an elongated medical device from a snail pack by pulling the elongated medical device from the sheath of the snail pack along the longitudinal axis of the elongated medical device may cause the medical device to interact with (e.g. slide against) an inner surface of the sheath, which may adversely impact an outer coating of the elongated medical device. While hydrating the elongated medical device prior to removing the elongated medical device from the outer sheath of the snail pack may help protect the outer coating of the elongated medical device during removal of the elongated medical device from the sheath, the hydration process (via immersion of the snail pack and device in a container of hydration liquid) may be time consuming. For example, given the positioning of the elongated medical device within the lengthy coiled sheath of the snail pack, the sheath may act to partially or entirely fluidically screen portions of the elongated medical device. A relatively long amount of time may be required for the hydrating fluid to flow into the lumen of the sheath, where the elongated medical device is housed, to hydrate an entire length of the elongated medical device. While some snail packs include a flush luer at one end (e.g., a threaded connection configured to mate with a syringe) in order to facilitate the injection of a hydrating fluid into the lumen of the sheath, the injection of a hydrating fluid into the sheath of the snail pack using the flush luer is an added step in the preparation for a medical procedure.

In some cases, an elongated medical device may be hydrated after it is removed from the medical device package. For example, the elongated medical device may be soaked in a hydrating fluid (e.g., a saline solution) in order to activate a hydrophilic coating on an outer surface of the elongated medical device. A clinician may remove the elongated medical device from a medical device package for purposes of hydration, after which the clinician, in the interest of easier manipulation of the elongated medical device, may return the length of the elongated medical device to the medical device package to await the eventual medical use. If the medical device package is a snail pack, this may require that the elongated medical device be removed from the snail pack, threaded back into the snail pack, and then again removed from the snail pack before the elongated medical device is used for a medical procedure, with each removal/reception step carrying a chance of affecting the structural integrity of the elongated medical device.

Further, each of these steps (hydrating prior to removal from the snail pack, hydrating after the snail removal, coiling the medical device after removal from the snail pack, and the like) may take a number of seconds, such that a complete process of prepping an elongated medical device for a medical procedure may take a number of minutes. In situations where a plurality of elongated medical devices (e.g., 5 to 12 elongated medical device) are used for a single medical procedure, the entire process may stretch out even longer. In a medical environment where saving seconds and minutes can have substantial positive benefits, it may be advantageous to expedite this process.

Aspects of this disclosure relate to a medical device package comprising a tray that defines a recess configured to receive an elongated medical device while the medical device is in a coiled state (also referred to herein as a coiled configuration). The medical device package may be referred to as a tray-type medical device package. The medical device package may further comprise a lip that extends out over the recess and covers a portion of the recess. The tray and lip together may define a mouth of the recess. Further, the tray and lip may define an opening that exposes the elongated medical device when the elongated medical device is received in the recess. The mouth is configured to facilitate the removal of the elongated medical device from the recess through the opening while the medical device is in the coiled state. The mouth and opening are configured to facilitate the removal of the elongated medical device from the recess in a lateral direction while the medical device is in the coiled state. The lateral direction can be, for example, lateral relative to the longitudinal axis of the coiled elongated medical device, and is not perpendicular to a bottom surface of the recess. The lip extends over a portion of the recess, and, in this way, may be configured to prevent the medical device from being lifted up out of the recess in a direction perpendicular to a bottom surface of the recess.

Configuring the medical device package to allow the lateral removal of the elongated medical device from the recess in the coiled state may provide time savings to a preparation process used to prepare the elongated medical device for use a medical procedure. For example, the tray-type medical device packages described herein that are configured to house an elongated medical device in a coiled state and allow the elongated medical device to be removed from the package in the coiled state may reduce the amount of time required to remove the medical device from the package, e.g., as compared to a snail pack. Further, the tray-type medical device packages described herein may reduce the amount of time required to perform tasks with the medical device in the coiled state, the tasks including the flushing of one or more lumens of the elongated medical device, hydrating the elongated medical device, lubricating an outer surface of the elongated medical device, assembly or attachment of accessories to the elongated medical device, placement of the elongated medical device into a hydration container (e.g., a saline bowl or bath), and inspection of the elongated medical device. The tray-type medical packages described herein may reduce the amount of handling of the elongated medical device required to perform the foregoing tasks, such as by reducing or eliminating repeated coiling and uncoiling of the elongated medical device, or reducing or eliminating the need to unload and reload the elongated medical device from an outer sheath, as may be done in a snail pack medical device package.

The tray-type medical device packages described herein may be configured to fluidically expose the entirety of an elongated medical device stored therein when the elongated medical device is received in a recess of the respective medical device package. The medical device package may be further configured to fit within a hydration container. Configuring the medical device package to fit within a hydration container while fluidically exposing the entirety of the elongated medical device may allow a clinician to relatively quickly hydrate an elongated medical device, providing time savings to the clinician. For example, a clinician may fully hydrate the elongated medical device, e.g., to activate a hydrophilic coating of the medical device, while the elongated medical device is still within the tray. As an example, the clinician may remove the tray in which the elongated medical device is housed from a sealed pouch and place the tray within a hydration container filled with a saline solution or another hydrating fluid. In some examples, the tray may include drain holes configured to drain a liquid within the tray, providing further time savings as such a medical device package could be removed from a hydration container and placed on a surface to drain while the clinician attends to other activities.

In contrast to the medical device packages described herein, fully hydrating an elongated medical device housed in a snail pack by placing the medical device package in which the elongated medical device is housed into a hydration container may be more time consuming because the hydration fluid may take longer to migrate into the inner lumen of the sheath to hydrate a full length of the elongated medical device. Further, with the medical device packages described herein, no special apparatuses, such as syringes, are needed to hydrate the medical device while it is still in its packaging. This may further simplify the preparation for a medical procedure.

Aspects of the present disclosure relate to configuring a plurality of medical device packages to interlock with each other (e.g., to nest together or form a stable stack when stacked upon each other) and form a stack of packages while maintaining a fluidic exposure of the elongated medical device received by the respective medical device package. For example, a tray-type medical device package may be configured with a profile or set of features that are configured to mate (e.g., mate in interlocking fashion) with another medical device package, thereby allowing a plurality of medical device packages to be fixed relative to each other in a stacked orientation. This may allow a plurality of medical device packages to be placed in a hydration container to concurrently hydrate a received plurality of elongated medical devices. In some examples, the plurality of medical device packages may be configured to mate such that a stack of numerous medical device packages (e.g., a dozen medical device packages) may be lifted, placed in a hydration container, and moved by only handling a minority (or other subset) of medical device packages of the stack (e.g., by only holding the bottom medical device package within the stack or the bottom two or three device packages within the stack) while maintaining a low likelihood that the stack of medical device packages will become unbalanced or that the medical device packages will separate from each other.

Figure 2:
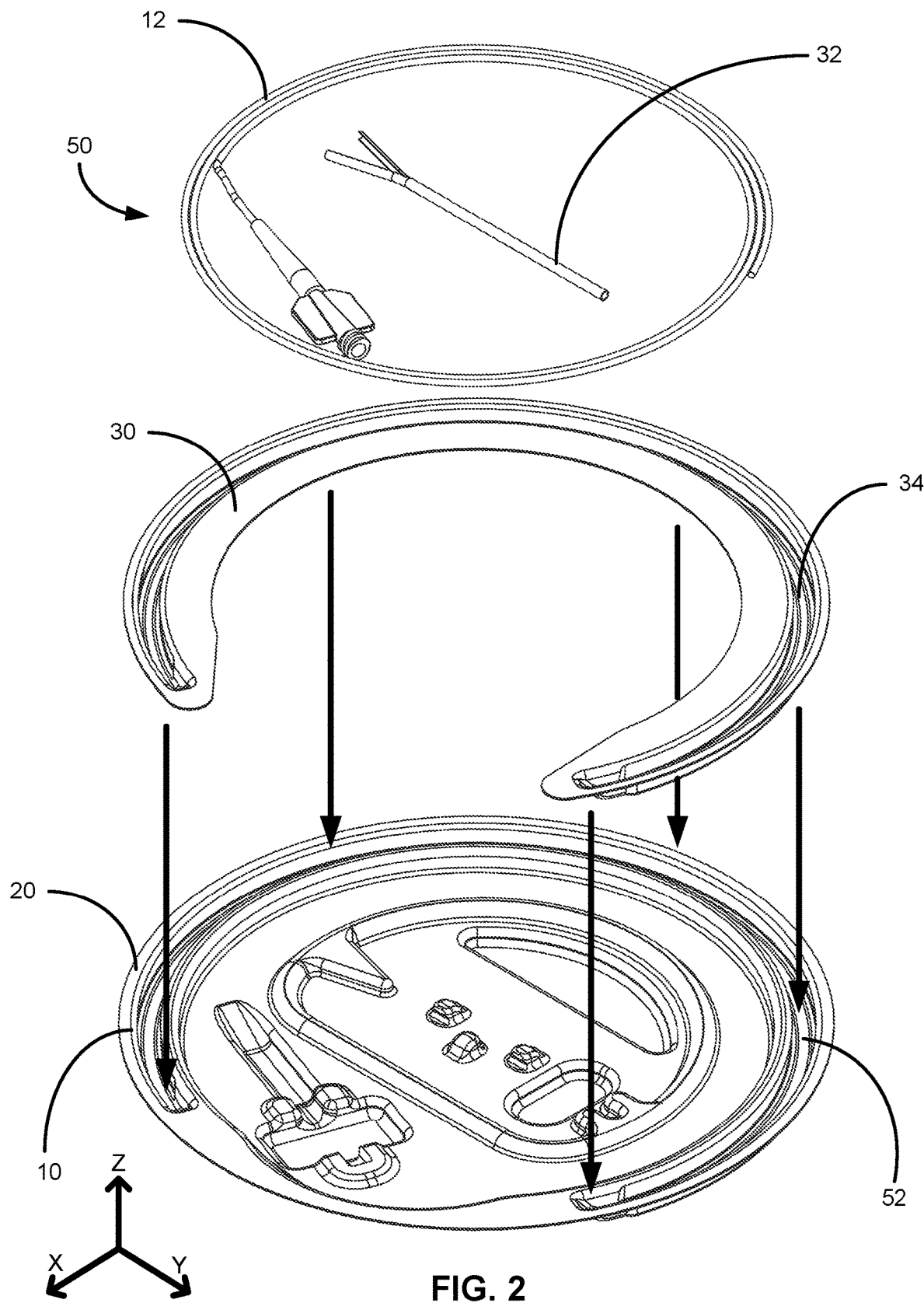
FIG. 2 depicts an exploded perspective view of the medical device package, elongated medical device and medical component shown in FIG. 1.

FIG. 1 illustrates a perspective view of an example tray-type medical device package 10 configured to receive and house elongated medical device 12 in a coiled state (e.g., in a coiled shape 50, as shown in FIG. 2) in a channel or recess 14. Elongated medical device 12 can be any suitable medical device, such as, but not limited to, a catheter, a guidewire, an implant delivery system such as a stent delivery device, an instrument such as a thrombectomy device located at the end of an elongated member such as a wire, hypotube, a combination of wire and hypotube, an electrically conductive lead, an optical fiber, a catheter-deliverable heart valve, or another elongated vascular device. FIG. 1 depicts orthogonal x-y-z axes which are referenced herein.

Medical device package 10 includes a package body which can comprise a tray 20, which defines the channel or recess 14, and lip 30 that defines wall 32. Lip 30 extends over a portion of recess 14 and covers a portion of recess 14, which may help retain medical device 12 in recess 14. Medical device package 10 may include opening 16 that exposes elongated medical device 12 within recess 14. Tray 20 may define major surface 42. In some examples, major surface 42 may be generally flat along an x-y plane (e.g., as depicted in FIG. 6B), which may allow tray 20 to be relatively stable when it is sitting on a flat surface. In the example shown in FIG. 1, opening 16 exposes portions of tray 20 that store/retain medical components, such as elongated medical device 12. As discussed herein, exposing portions/components of medical device package 10 may include fluidically exposing (e.g., such that fluids may freely flow into and out of exposed areas of medical device package 10 through opening 16 when medical device package 10 is, for example, submerged in a fluid), visually exposing (e.g., such that exposed portions/components are readily viewable through opening 16 for inspection along at least a single surface of a respective exposed portion/component), and/or exposing a component to removal (e.g., such that components that are exposed may be therein physically removed through opening 16). Opening 16 may be configured to expose tray 20 along an x-y plane. In some examples, opening 16 may expose major surface 42 of tray 20. In the example shown in FIG. 1, tray 20 and lip 30 cooperate to define opening 16.

Lip 30 is a structure that extends over and covers a portion of recess 14 of tray 20, which may help retain elongated medical device 12 in recess 14. For example, lip 30 may act as a barricade that helps prevent elongated medical device from falling out of recess 14 in the z-axis direction (orthogonal x-y-z axes are shown in the figures for ease of description only). In examples in which tray 20 defines a circular recess 14, lip 30 may be configured to cover about 90° to about 315° of the recess. For example, lip 30 may define most (e.g., 300° or 315°) of a circle. In such examples, lip 30 may be configured to only provide wall 32 that covers recess 14 for a portion of recess 14 around the perimeter of tray 20, as discussed in further detail with respect to FIG. 7.

Lip 30 and tray 20 may define mouth 40, which extends in between lip 30 and tray 20 along the z-axis. Mouth 40 of medical device package 10 may be configured to facilitate the removal of elongated medical device 12 from tray 20 in the coiled state. For example, a clinician may reach through opening 16, grasp elongated medical device 12 that is within recess 14 of medical device package 10 in the coiled state, and remove elongated medical device 12 from recess 14 through opening 16 and mouth 40 while elongated medical device 12 is still in the coiled state. As discussed above, a medical device package that facilitates removal of elongated medical device 12 from the package in the coiled state may have performance benefits for elongated medical device 12 and time benefits for use of elongated medical device 12.

Figure 8:
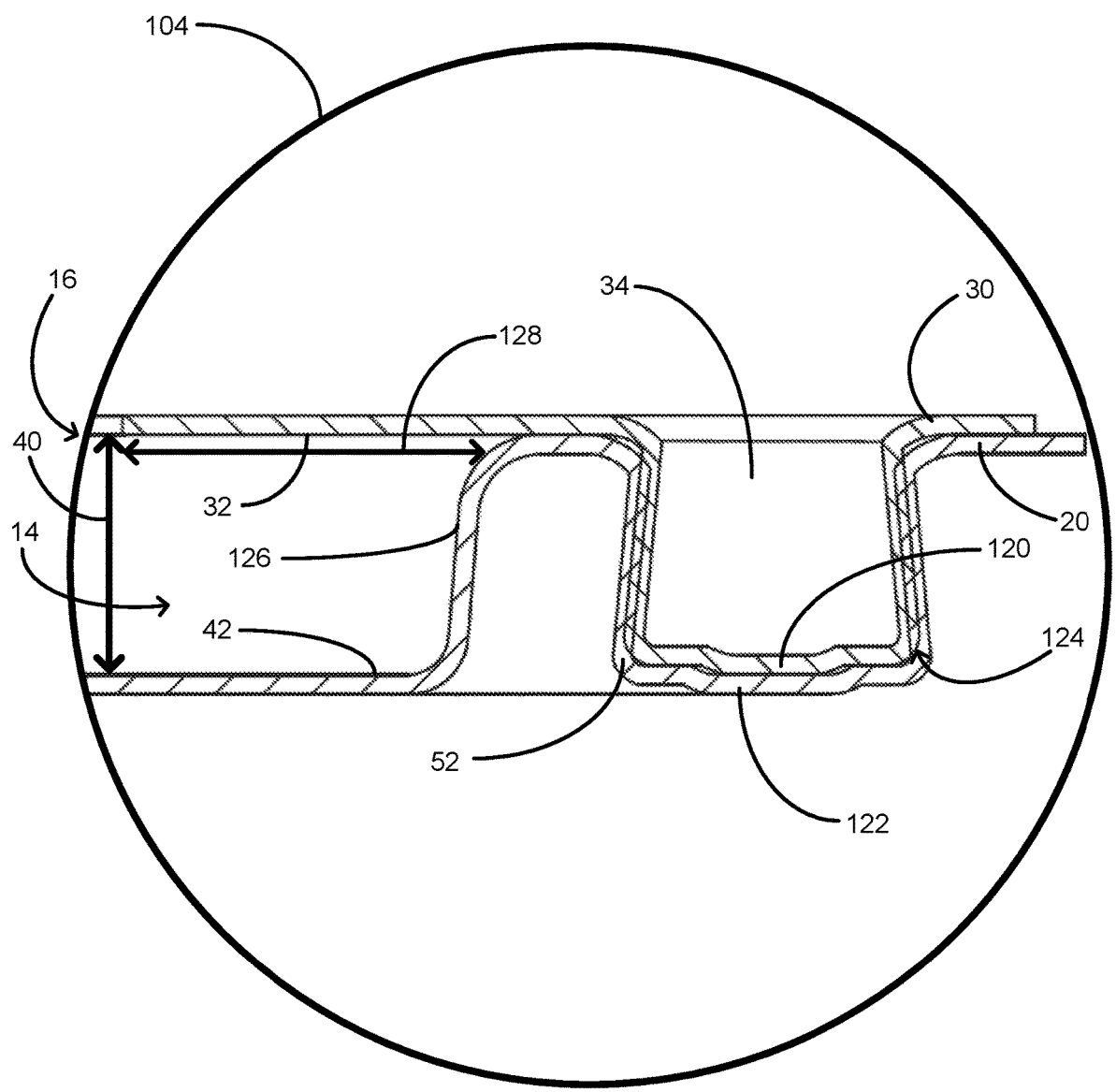
FIG. 8 depicts a cross-sectional detail view of an example tray receiving an example lip, where the cross-section is taken along line 92-92 of FIG. 6A and the detail is within circle 104 of FIG. 6B.
Figure 8:
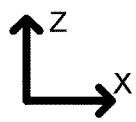

In some examples, recess 14 of medical device package 10 may be a cavity defined by two or more walls, as depicted in FIG. 8. As such, when elongated medical device 12 is received by recess 14, elongated medical device may be retained in approximately 270° (e.g., as measured radially around an outer perimeter of elongated medical device 12) and exposed in approximately 90° (e.g., as measured radially around an outer perimeter of elongated medical device 12). When elongated medical device 12 is received by recess 14, elongated medical device 12 may be predominantly or exclusively accessible/exposed by opening 16 through mouth 40 to the interior/inside of elongated medical device 12/medical device package 10 along an x-y plane (at least along an initial removal path of the elongated medical device 12, after which the removal path may define a subsequent component in the z-axis direction due to user preference and/or the presence of package feature(s) that make departure from motion in the x-y plane advantageous/necessary), though elongated medical device 12 may also be exposed along the z-axis along a portion of tray 20 in which lip 30 recedes to an outer perimeter of tray 20 or is otherwise absent. In some examples, tray 20 may define two walls of recess 14 and lip 30 may cover recess 14 with wall 32 opposite major surface 42 of tray 20. Elongated medical device 12 may press against an out radial wall of recess 14 in the coiled state as the elongated medical device 12 attempts to uncoil and elongated along a longitudinal axis of elongated medical device 12.

In some examples, lip 30 and tray 20 may be manufactured as a single unitary structure. In other examples, lip 30 may be manufactured as a separate component from tray 20. In such examples, tray 20 may be configured to receive lip 30 to define opening 16 and mouth 40. For example, lip 30 may be configured to be a hollow circular, partially circular or semi-circular component. Whether lip 30 and tray 20 are manufactured as a single unitary structure or are manufactured as separate components, lip 30 and tray 20 may be configured to be either moveable relative to each other or fixed relative to each other. For example, lip 30 may be attached to tray 20 such that lip 30 is hinged as in a clamshell configuration. In some examples, lip 30 and tray 20 may be configured to be moveable relative to each other when medical device package 10 has received elongated medical device 12 (e.g., rather than lip 30 and tray 20 only being "moveable" and that lip 30 and tray 20 are assembled together in preparation of receiving elongated medical device 10).

In examples in which lip 30 is configured to be a separate manufactured component from tray 20, lip 30 may be configured to attach to tray 20 to prevent lip 30 from separating from tray 20 during use of medical device package 10. For example, a channel of tray 20 (e.g., channel 52 shown in FIG. 2) may be configured to receive ridge 34 of lip 30. The channel of tray 20 may receive ridge 34 with an interference fit as depicted in FIG. 8. In these examples, tray 20 may be configured to define the location of lip 30 through the specific configuration of the channel. For example, the channel may be configured to extend around most (e.g., 305° or 320° of) a perimeter of tray 20, such that wall 32 of lip 30 extends around the perimeter of tray 20 near the majority of the perimeter that includes the channel. In this way, the channel of tray 20 may be configured to define the location of mouth 40 of medical device package 10.

In other examples, lip 30 may be configured to attach to tray 20 in a pseudo-permanent fashion, such that lip 30 and tray 20 may not be separated without physically damaging medical device package 10. For example, lip 30 may be welded, fused, glued, or pressed into tray 20 such that lip 30 is configured to not separate from tray 20.

In the example shown in FIG. 1, tray 20 may define ramp 46, which may facilitate the removal of elongated medical device 12 from recess 14 while medical device 12 is in a coiled state. Ramp 46 may be a sloped surface that extends up through the z-axis from major surface 42 of tray 20 to a top surface of the tray (e.g., the surface that defines channel of tray 20 and therein receives lip 30). It is to be understood that the specific shape and dimensions of ramp 46 as depicted in FIG. 1 are for purposes of illustration only, and that ramp 46 may comprise other shapes and angles that define a surface that smoothly (e.g., without sharp angles) connects major surface 42 of tray 20 to the surface of the channel of tray 20 as depicted in FIG. 1. In some examples, a clinician may place a few fingers along major surface 42 of tray 20 of medical device package 10 that has received elongated medical device 12, and may grab and remove elongated medical device 12 from recess 14 while elongated medical device 12 is in the coiled state merely by pulling the grabbing fingers back and up ramp 46.

This motion may cause the portion of elongated medical device 12 covered by lip 30 to exit recess 14 in a lateral direction, e.g., through mouth 40. Thus, ramp 46 may help guide the removal of elongated medical device 12 through mouth 40 by providing an intuitive surface for the clinician to follow to apply the proper pulling force in the proper direction to remove elongated medical device 12 (in the coiled state) through mouth 40.

Accordingly, medical device package 10 may define a removal path of elongated medical device 12 that extends laterally (e.g. at least in part in the x-y direction) from recess 14 to a central region of tray 20 or package body, which central region can be bounded at least in part by the channel or recess 14. As will be explained in greater detail herein, the central region can comprise one or more physical surfaces or features, e.g. for retaining additional components that may be used along with elongated medical device 12. Alternatively, the central region can consist wholly or in part of a void or opening such that tray 20 has the overall configuration of a hoop.

In some examples elongated medical device 12 may include a component, such as a stent, a wire-mounted stent or another implantable medical device, a hub 18, and/or some another medical component. While it is to be understood that elongated medical system 12 may include any such known medical component or even numerous such medical components on one elongated medical device 12, for purpose of clarity elongated medical system 12 is discussed herein predominantly as only including hub 18 at a proximal end of elongated medical device 12.

In examples in which elongated medical device 12 includes a medical component, medical device package 10 may include a retention system configured to retain the medical component. For example, in the depicted medical device package 10, tray 20 is configured to receive hub 18, e.g., via a snap fit. The retention system may include indentation 36 and/or retention members 24A-24C (collectively "retention members 24"). In some examples, indentation 36 and retention members 24 may be features defined by tray 20. Indentation 36 may be, for example, a physical depression within a surface of tray 20 that is configured to receive hub 18 (e.g., receive hub 18 such that hub 18 is partially "submerged" into major surface 42 of tray 20). Indentation 36 may be configured to be generally shaped like hub 18 (or other medical component). Indentation 36 may be configured to receive hub 18 with an interference fit or any other suitable technique.

In other examples, retention members 24 may be projections from tray 20. Similar to indentation 36, retention members 24 may be configured to receive hub 18 with an interference fit. In other examples (not depicted), retention members 24 may instead be configured to clip to, enclose, or otherwise engage hub 18 to mechanically retain hub 18 at location 38. Indentation 36 and retention members 24 may retain hub 18 at location 38. Location 38 may be configured to be spatially distinct from the coiled state to allow easy inspection or secure storage of hub 18. By configuring indentation location 38 to be spatially distinct for easy inspection, medical device package 10 may provide time savings to clinicians.

In some examples, medical device package 10 may be configured to retain one or more other medical components related to elongated medical device 12. For example, as depicted in FIG. 1, tray 20 may be configured to retain introducer 44 for using elongated medical device 12 in a medical procedure. Tray 20 may be configured to receive and retain introducer 44 or another medical component (e.g. one which is shorter in length than elongated medical device 12) via a snap fit or any other suitable mechanism. In the example shown in FIG. 1, tray 20 is configured to retain introducer 44 or another medical component via one or more retention members 26A-26C (collectively, "retention members 26"). Retention members 26 may be configured to include physical protrusions that extend away from major surface 42 of tray 20 towards lip 30 to generally define the shape of medical components. In this way, retention members 26 may be configured to receive a medical component and retain the medical component via a snap fit by having the medical components pushed between retention members 26 in a particular configuration.

In some examples, medical device package 10 may be configured to hold or retain a portion (e.g., a distal portion and/or distal tip) of elongated medical device 12 in a configuration and/or location apart from the coiled configuration that prevails along the majority of elongated medical device 12 in recess 14. For example, tray 20 may be configured (e.g. in the central region thereof) to hold the distal portion or tip of elongated medical device 12 in a straight configuration, or in a curved configuration different from the coiled loop(s) of elongated medical device 12 in recess 14. In some such examples, a D-shaped planform may be useful for tray 20 to accommodate the distal portion or tip packaged in this manner. A molded channel and/or one or more retention members (such as retention members 26) may be used to hold the distal portion or tip in the desired straight or differently-curved configuration. To remove medical device 12 when packaged in this manner, the user may first remove the distal portion or tip from its straight or differently-curved storage location, and then remove medical device 12 from recess 14 and tray 20 in the typical manner as described elsewhere herein. Note that when a portion such as the distal tip or distal portion of elongated medical device 12 is held by medical device package 10 in such a straight or differently-curved configuration, elongated medical device 12 itself is nonetheless considered to be in a coiled configuration.

Medical device package 10 may include one or more other features to facilitate use of package 10 during a medical procedure. For example, in some examples, medical device package 10 may include writing surface 22, which may be a surface that is configured to be written on by a clinician (e.g., with medical or procedural or administration information). Writing surface 22 may be configured to be a relatively flat surface on tray 20. Writing surface 20 may be configured to retain ink of writing instruments (e.g., retain ink such that ink of writing instruments cannot be easily smeared or removed after such ink is on writing surface 22). Write surface 22 may be configured such that it is visually unobscured by elongated medical device 12 (e.g., unobscured when elongated medical device 12 is received by recess 14 in the coiled state) or a medical component (e.g., introducer 44) that is received by medical device package 10.

Tray 20 and lip 30 may be formed from any suitable material, such as but not limited to, polyethylene terephthalate glycol-modified (PETG), Tritan, or other suitable polymers or materials. In some examples, medical device package 10 may be configured to withstand sterilization procedures for elongated medical device 12. For example, medical device package 10 may be formed from a material configured to withstand being exposed to a predetermined sterilization temperature for a predetermined period of time. For example, the predetermined sterilization temperature may be about 50° C. In some examples, the predetermined period of time may be about 1 second, about 10 seconds, about 1 minute, about 30 minutes, about 1 hour, about 2 hours, or more than 2 hours. In some examples, in addition to, or instead of, exposing medical device package 10 and received elongated medical device 12 to the predetermined sterilization temperature, medical device package 10 may be configured to withstand other sterilization techniques. For example, medical device package 10 may be configured to withstand microwave, steam, ethylene oxide or ozone sterilization, or other sterilization techniques. In some examples, the sterilization may be performed after sealing tray 20, lip 30, and elongated medical device 12 in a pouch of medical device package 10. In other examples, the sterilization may be performed before sealing elongated medical device 12 in a pouch of medical device package 10.

In some examples, all or part of medical device package 10 may be manufactured from an opaque or transparent material. For example, in some examples lip 30 may be configured to be transparent, or both lip 30 and tray 20 may be configured to be transparent. Configuring medical device package 10 to be opaque or transparent may provide one or more advantages. For example, if elongated medical device 12 may be inspected when elongated medical device 12 is in a coiled state within recess 14, elongated medical device 12 may require less handling prior to use in a medical procedure.

FIG. 2 depicts an exploded perspective view of medical device package 10, elongated medical device 12, and introducer 44. As depicted in FIG. 2, elongated medical device 12 is in coiled state 50, in which elongated medical device 12 is arranged in a plurality of concentric loops, which may have substantially similar radii in some examples. The radii defined by medical device 12 in coiled state 50 may be selected to be equal to or less than a radius of recess 14, such that medical device 12 may be inserted in recess 14 when in coiled state 50. As discussed above, recess 14 is defined by walls that help retain medical device 12 in coiled state 50 when medical device 12 is in recess 14. Elongated medical device 12 may be configured to be uncoiled, e.g., to a straightened shape along a longitudinal axis of elongated medical device 12, after being removed from medical device package 10. FIG. 2 also depicts channel 52 of tray 20. As discussed above, channel 52 may be configured to extend around part of a perimeter of tray 20 (e.g., most of a perimeter or at least half of the perimeter), and may be configured to receive ridge 34 of lip 30 in order to fix lip 30 and tray 20 relative to each other.

Figure 3:
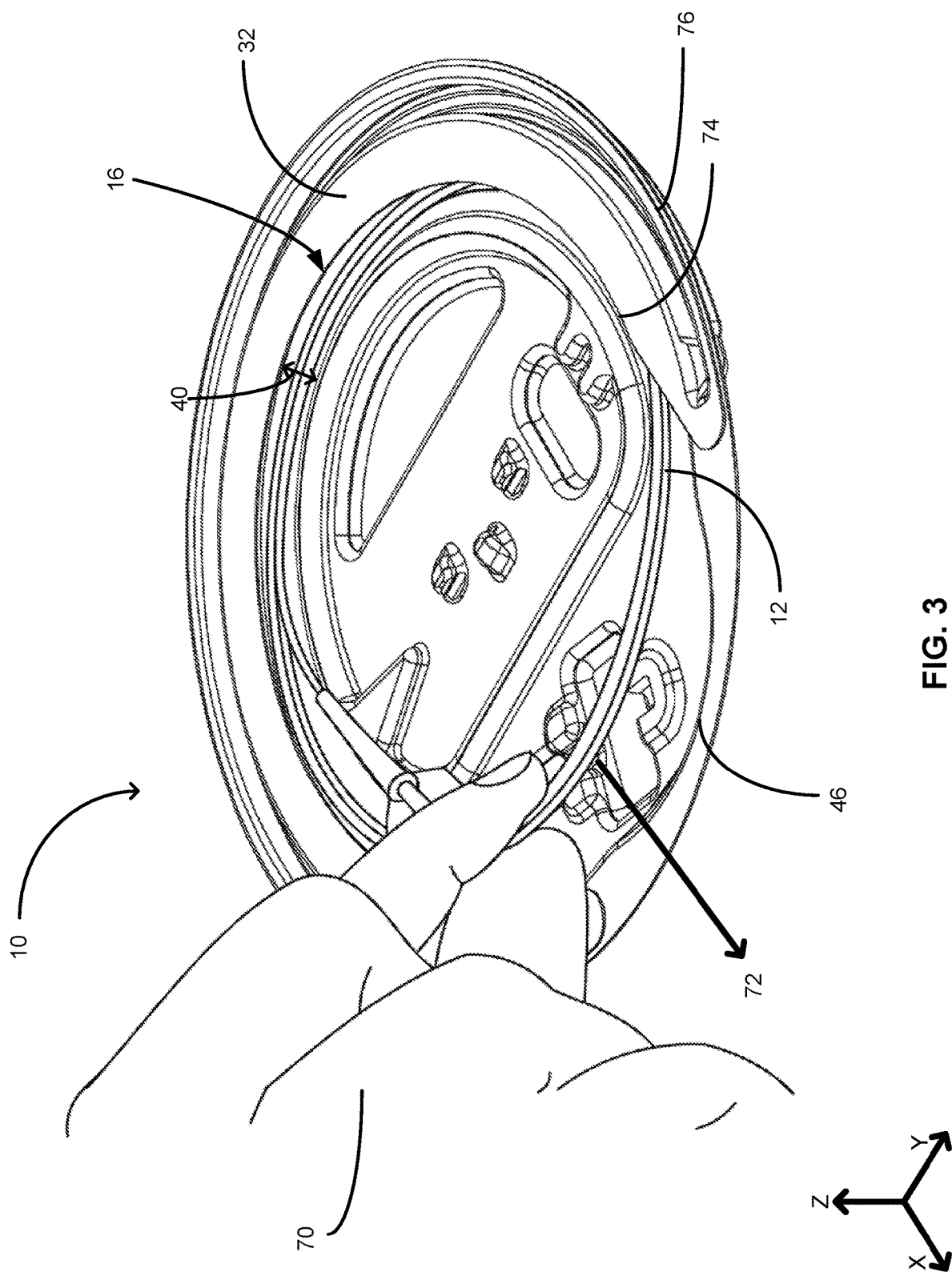
FIG. 3 depicts a perspective view of the elongated medical device being removed from the medical device package of FIG. 1.
Figure 4:
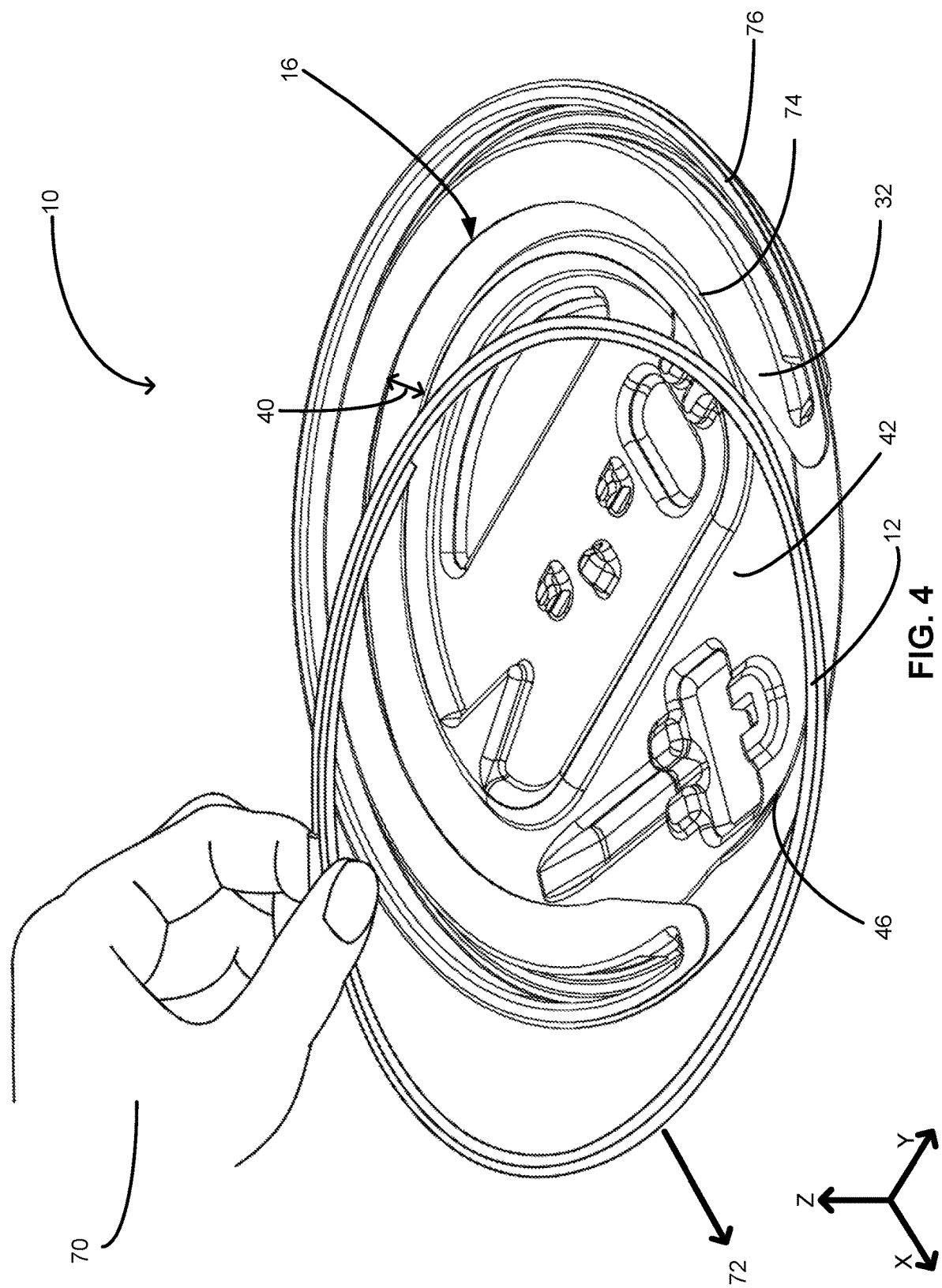
FIG. 4 depicts another perspective view of the elongated medical device being removed from the example medical device package of FIG. 1.

FIGS. 3 and 4 depict a perspective view of elongated medical device 12 being pulled from recess 14 of medical device package 10 through opening 16 in package 10 and a perspective view of elongated device 12 then being removed from medical device package 10 along a generally lateral direction 72, respectively. Elongated medical device 12 may be pulled by fingers of clinician 70. As shown in FIG. 3, clinician 70 may grasp elongated medical device 12 through opening 16. For example, clinician 70 may grasp elongated medical device 12 near ramp 46. In some examples, recess 14 may be configured to only expose elongated medical device 12 to the hand of clinician 70 near ramp 46, as wall 32 of lip 30 may block the hand of clinician 70 from readily grasping the part of elongated medical device 12 covered by lip 30. For example, mouth 40 may not be dimensioned to allow fingers of clinician 70 to extend through mouth 40 to access the part of elongated medical device 12 covered by lip 30.

Medical device package 10 may define mouth 40 and/or opening 16 to facilitate the removal of elongated medical device 12 in lateral direction 72. Lateral direction 72 may be lateral relative to the longitudinal axis of elongated medical device 12. Lateral direction 72 may be predominantly or exclusively along an x-y plane. In some examples, medical device package 10 may further define mouth 40 and/or opening 16 to facilitate the removal of elongated medical device 12 in a direction away from major surface 42 of tray 20 (e.g., as clinician brings elongated medical device 12 "up and out" of medical device package 10).

Lip 30 defines an inner edge 74, which may be configured to curl away (or be bent or deflected away) from major surface 42 of tray 20 by being manufactured with a radius that is greater than the radius of outer edge 76 of tray 20 minus the linear distance between outer edge 76 and inner edge 74. Curling inner edge 74 away from major surface 42 may effectively increase the height of mouth 40. For example, if outer edge 76 has a radius of 9 centimeters and there is 1.5 centimeters between outer edge 76 and inner edge 74, an inner edge 74 may be manufactured with a radius of 8 centimeters (e.g., a difference of 1 centimeters in relation to the outer edge 76, which is less than the actual linear difference when viewed parallel to major surface 42 of tray 20) to configure inner edge 74 to curl, bend or deflect away from tray 20 in a z-axis direction. Configuring inner edge 74 of lip 30 to curl away from major surface 42 of tray 20 may allow clinician 70 to more easily pull elongated medical device 12 "up" (in a z-axis direction) away from tray 20 as clinician 70 is removing elongated medical device 12 (e.g., as medical device 12 may be less likely to interact with inner edge 74 (e.g., catching on inner edge 74) during the removal of elongated medical device 12 through mouth 40.

In some examples, lip 30 is configured to be flexible to further facilitate the removal of elongated medical device 12. For example, lip 30 may be configured to flex relative to tray 20 (e.g., in a z-axis direction) in response to clinician 70 reaching into mouth 40 to grasp elongated medical device 12 or in response to elongated medical device 12 being lifted out of recess 14 in a z-axis direction. Lip 30 may be configured to flex due to, for example, the material that lip 30 is manufactured with and/or by the thickness of lip 30. Configuring lip 30 to be flexible may allow mouth 40 to further open (in the z-axis direction) and become relatively larger in response to the forces of elongated medical device 12 being removed from recess 14, and to maintain a resting position that allows mouth 40 to maintain a smaller size in the absence of a force pulling lip 30 away from tray 20. In this way, a flexible lip 30 may provide benefits to medical device package 10 in both retaining elongated medical device 12 in recess 14 and facilitating the removal of elongated medical device 12. Further, configuring lip 30 to be flexible may make it possible and/or more comfortable for clinician 70 to reach into recess 14. In some examples, wall 32 of lip 30 is flexible, while the rest of lip 30 is relatively less flexible (e.g., as wall 32 gets thinner as wall 32 extends radially in towards inner edge 74).

The depicted lip 30 and wall 32 provide a single continuous structure extending along a portion of the periphery of tray 20, and inward or laterally over recess 14. Alternatively, lip 30 and/or wall 32 may be interrupted by one or more gaps therein, such that recess 14 and/or elongated medical device 12 is wholly or partially exposed in such gap(s). Lip 30 and/or wall 32 may take the form of a plurality of inwardly or laterally extending tabs separated by gaps. In such a case, the gaps may individually and/or collectively be smaller (e.g., narrower) than the tabs when viewed in planform (e.g., view depicted in FIG. 5), or larger or wider than the tabs, or about the same size as the tabs. The tabs may be bendable or deflectable in the z-direction to facilitate removal of elongated medical device 12 from tray 20. When lip 30 or wall 32 is interrupted or takes the form of a plurality of discrete tabs, mouth 14 may nonetheless be considered to extend continuously along the entire series of tabs and gaps.

Figure 5:
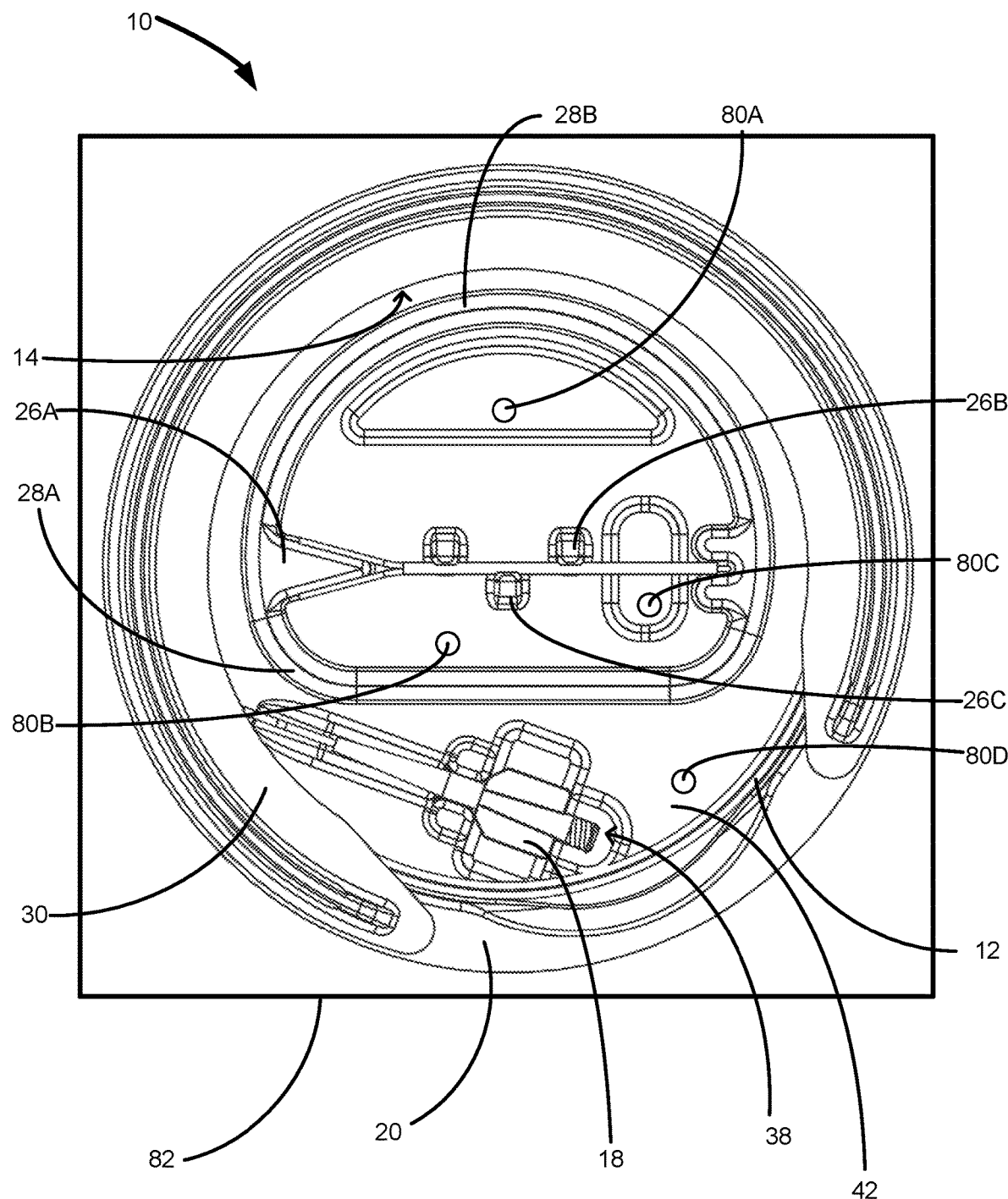
FIG. 5 depicts a top view of the medical device package, elongated medical device, and medical component of FIG. 1.

FIG. 5 depicts a top view of medical device package 10 that has received elongated medical device 12 and introducer 44. As depicted in FIG. 5, tray 20 is configured to receive a portion of elongated medical device, e.g., hub 18 in the example of FIG. 5, at location 38. Location 38 is visually removed from coiled elongated medical device 12, which may allow a clinician to easily find the retained portion of elongated medical device 12. In some cases, for example, a clinician may inspect the medical component held at location 38 prior to using medical device 12. For example, if the medical component is a stent or another medical component within an inner lumen of device 12, the clinician may inspect the stent prior to implanting it in a patient. Placing and securing the portion of elongated medical device 12 including the stent or other component in location 38 may facilitate relatively quick inspection by a clinician because, for example, the clinician does not need to pull the entire medical device 12 out of recess 14 to inspect the component or does not need to hunt for the portion of medical device 12 including the stent or other component to be inspected.

As depicted in FIG. 5, in some examples, medical device package 10 may be configured to have a generally circular planform, the planform being as viewed in the x-y plane. In some examples, medical device packages 10 may have circular planforms that are sized to fit in respective hydration containers (e.g., if a hydration container has a 20 centimeter diameter, medical device packages 10 may be configured with a circular cross section with an 18 centimeter diameter). In other medical device package 10 may be configured to have a non-circular planform, such as a D-shaped planform, an ovaloid planform, a quadrilateral planform, or the like. In these examples, however, tray 20 may define a circular or ovoid recess 14 configured to receive medical device 12 in the coiled shape 50.

In some examples, tray 20 of medical device package 10 may be configured with one or more drain holes 80A-D (collectively, "drain holes 80"). Drain holes 80 may be holes that are punched through an entire thickness of a bottom surface of tray 20. In some examples, drain holes 80 may be configured to be located on any portion of major surface 42 of tray 20 that may independently collect a non-nominal amount liquid. Drain holes 80 may be configured to drain any liquid, such as a hydration liquid, from tray 20. For example, after tray 20 has been submerged in or otherwise placed in a hydration container with hydrating fluid, some fluid may remain in tray 20; drain holes 80 may facilitate the removal of this remaining fluid from tray 20. Configuring tray 20 to include drain holes 80 that are configured to drain liquid from tray 20 may result in medical device package 10 drying faster following hydration of elongated medical device 12, providing time benefits to clinician.

Tray 20 may include one or more strengthening ribs 28A-28B (collectively, "strengthening ribs 28"). Strengthening ribs 28 may be configured to strengthen major surface 42 of tray 20. In some examples, strengthening ribs 28 may be configured to strengthen the entirety of medical device package 10 against bending forces, reducing the chances of undesired deformation of medical device package 10 and/or elongated medical device 12. In certain examples, strengthening ribs 28 may be configured to mate with other medical device packages 10 that are substantially similar to medical device package 10, such that a plurality of substantially similar medical device packages 10 may be interlocked and stacked (in a z-axis direction) in a stable manner (e.g., such that the stack is unlikely to fall in response to a nominal force such as being struck by a person moving at a walking pace, or inertial forces present when the stack is carried by a person moving at a walking pace). Strengthening ribs 28 may also be configured to cooperate with retention members 26, such that strengthening ribs 28 may share features or surfaces with retention members 26. For example, strengthening rib 28 may be configured to concurrently retain medical components and strengthen tray 20.

As depicted in FIG. 5, elongated medical device 12 is received within recess 14 in the coiled shape 50. Elongated medical device 12 may be held in the coiled state using any suitable technique. In some examples, due to the materials and configuration of elongated medical device 12, medical device 12 may tend to uncoil, e.g., extend to a generally straight configuration, when unconstrained. In such examples, this "self-expanding" or "self-uncoiling" property—the propensity to extend straight along its longitudinal axis—may result in a coiled elongated medical device 12 expanding against outer walls defining recess 14 without the aid of any attachment or retention elements (e.g., any retention system other than the walls of recess 14).

In other examples, elongated medical device 12 may be configured to maintain the coiled state when unconstrained, e.g., when released within recess 14 without further retention features. In such examples, elongated medical device 12 may be retained within a shallower recess 14 and/or may not expand against the outer walls defining recess 14. For example, elongated medical device 12 may be retained within recess 14 with a slight ridge rising up from major surface 42 of tray 20 (not depicted), and/or elongated medical device 12 may be retained within recess 14 by a slight curl or bend of inner edge 74 of lip 30 towards major surface 42 of tray 20. Curling or bending inner edge 74 towards major surface 42 may effectively decrease the height of mouth 40. As discussed above in the inverse (e.g., inner edge 74 curling or bending away rather than towards major surface 42), inner edge 74 may be configured to curl towards major surface 42 of tray 20 by being manufactured with a radius that is smaller than the radius of outer edge 76 minus the linear distance between outer edge 76 and inner edge 74. For example, if outer edge 76 has a radius of 9 centimeters and there is 1.5 centimeters between outer edge 76 and inner radius 74, inner radius may be manufactured with a radius of 7 centimeters (e.g., a difference of 2 centimeters in relation to the outer edge 76, which is greater than the actual linear difference when viewed parallel to major surface 42 of tray 20) to configured inner edge 74 to curl towards tray 20.

In some examples, medical device package 10 may include pouch 82, which houses tray 20, lip 30, and elongated medical device 12 housed within recess 14 of tray 20. Pouch 82 may include one or more of a woven panel, a non-woven panel, a plastic panel, a polymer film, a paper film, a coated paper film, a metalized polymer film, a foil, a tray, a thermoform, a two-piece clamshell, or a folded clamshell. After tray 20 and lip 30 and elongated medical device 12 are placed into a housing of pouch 82 (with device 12 in tray 20 and lip 30 connected to tray 20, e.g., as shown in FIG. 1) through an unsealed mouth of pouch 82 having, for example, three pre-sealed edges, pouch 82 may be sealed by sealing first and second peripheral edge regions of pouch 82 (e.g., where first and second peripheral edge regions are the two sides of the unsealed mouth). Pouch 82 may be included in the sterilization process as is discussed herein, such that medical device package 10 may be sterilized within pouch 82, whether before or after medical device package 10 is sealed within pouch 82. After medical device package 10 receives elongated medical device 12, the first and second peripheral edge regions may be sealed, for example, by thermal sealing. Impulse sealing may be used to expose at least one of the first or second peripheral edge regions to a predetermined sealing temperature that causes the first and second peripheral edge regions to seal, for example, by fusing or melting.

Figure 6A:
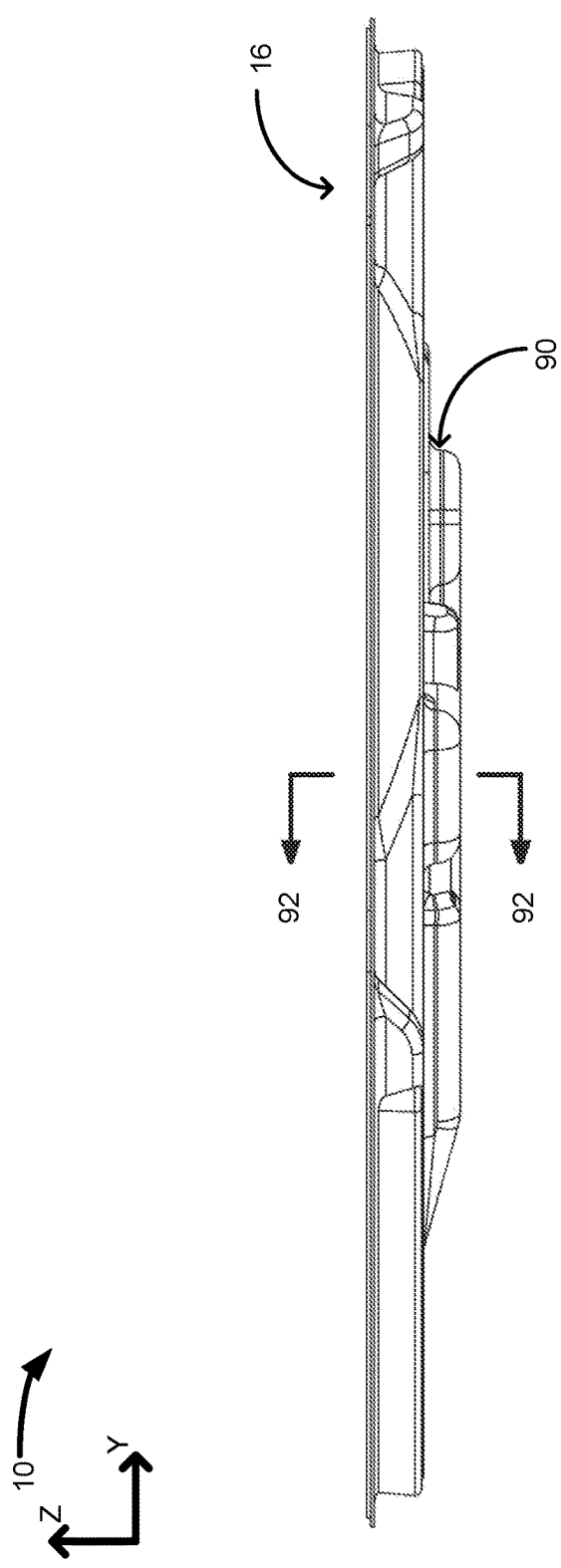
FIG. 6A depicts a side view of the medical device package of FIG. 1.
Figure 6B:
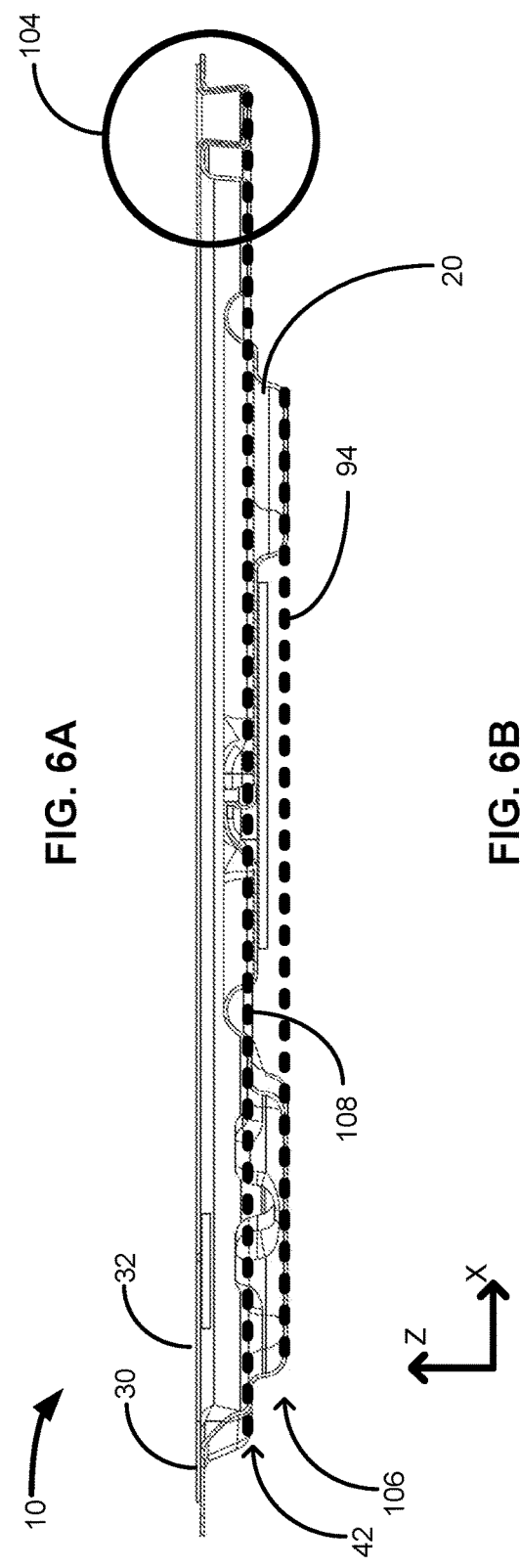
FIG. 6B depicts a cross-sectional side view of the medical device package of FIG. 6A, where the cross-section is taken along line 92-92 in FIG. 6A.

FIG. 6A depicts a side view of an example medical device package 10. FIG. 6A depicts the profile of medical device package 10 as seen in the y-z plane. In some examples, the profile of medical device package 10 may be configured to mate with another substantially similar medical device package 10. For example, bottom portion 90 of tray 20 may be configured to fit into opening 16 of another medical device package 10 having the same or similar configuration. In other examples (not depicted), only certain mating features of medical device packages 10 may be configured mate with respective corresponding mating features of other substantially similar medical device packages 10. In certain examples, the profile of medical device package 10 may be configured to mate with another substantially similar medical device package 10 such that, when mated, opening 16 still fluidically exposes each elongated medical device 12 received in respective recesses 14 of each substantially similar medical device package 10. In this way, a plurality of medical device packages 10 (e.g., a dozen medical device packages 10), each including an elongated medical device 12 received in respective recesses 14, may be stacked such that mating portions interlock in a hydration container such that a plurality of respective received elongated medical device 12 may be handled and hydrated concurrently.

FIG. 6A depicts cross-sectional cut 92. FIG. 6B depicts an example cross-sectional view from this cross-sectional cut 92 of an example medical device package 10. FIG. 6B depicts medical device package 10 as seen in the x-z plane that has not received elongated medical device 12. FIG. 6B depicts major surface 42 of tray 20. Major surface 42 may include surfaces of tray 20 that define plane 108. FIG. 6B also depicts detail view 104, which is depicted in FIG. 8. FIG. 6B depicts bottom surface 106 of tray 20. Bottom surface 106 of tray may include surfaces of tray 20 that define the plane 94.

Figure 7:
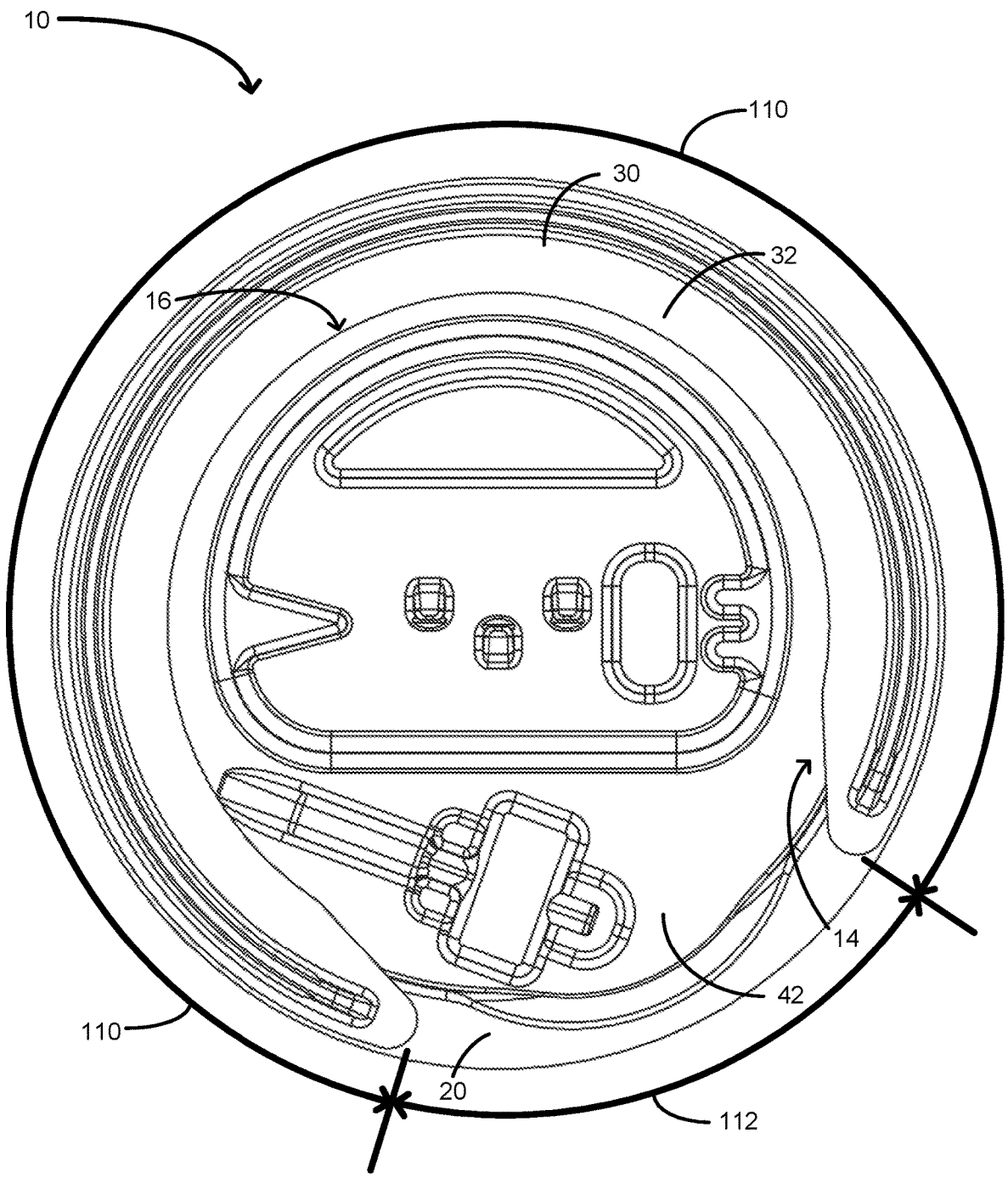
FIG. 7 depicts a top view of the medical device package of FIG. 1.

FIG. 7 depicts a top view of medical device package 10 as viewed along the z-axis at the x-y plane. Tray 20 includes a perimeter having first portion 110 and second portion 112, which together define the total perimeter. As shown in FIG. 7, in some examples, lip 30 is configured such that wall 32 of lip 30 extends over recess 14 for first portion 110 of the perimeter of tray 20, such that the part of recess 14 aligned with a second portion 112 of the perimeter is not partially covered by wall 32. In such examples, medical device package 10 may be configured to expose elongated medical device 12 to the interior of medical device package 10 in an x-y plane along an entirety of the perimeter of tray 20, while medical device package 10 is also configured to expose elongated medical device 12 along the z-axis opposite major surface 42 of tray 20 along second portion 112 of the perimeter of tray 20. Lip 30 may be configured to cover elongated medical device 12 opposite major surface 42 of tray 20 along first portion 110 of the perimeter of tray 20.

In other examples (not depicted), lip 30 and its wall 32 may extend around the entirety of perimeter of tray 20. In such examples, recess 14 may be covered by wall 32 (e.g., as in FIG. 8) around the entirety of the perimeter and second portion 112 of perimeter may not exist, such that elongated medical device 12 is never exposed opposite major surface 42 of tray 20. Instead, in such examples, recess 14 may be configured to only expose elongated medical device 12 through mouth 40 by opening 16 to interior of medical device package 10.

FIG. 8 depicts a cross-sectional detail view within circle 104 of an example tray 20 receiving an example lip 30. Circle 104 shown in FIG. 8 is not a physical part of medical device package 10, but rather is shown to illustrate how tray 20 and lip 30 of FIG. 8 correspond to FIG. 6B. FIG. 8 depicts the detail view as designed with an interference fit between channel 52 of tray 20 and ridge 34 of lip 30, though other means of tray 20 receiving lip 30 may be used in other examples (e.g., mating/interlocking components). When tray 20 and lip 30 are assembled, channel 52 and ridge 34 may not overlap as depicted, but may instead be configured to push together to create a stable fit. The amount of designed overlap 124 may define a strength of a fit between tray 20 and lip 30, such that a relatively larger overlap 124 may result in a stronger fit between tray 20 and lip 30, though a larger overlap 124 may also make it relatively more difficult to position ridge 34 of lip 30 in channel 52 of tray 20. In some examples, ridge 34 may be further configured with groove 120 that fits into groove 122 of channel 52. Grooves 120, 122 may be configured to further stabilize the fit between tray 20 and lip 30.

FIG. 8 depicts recess 14. Recess 14 may be defined by major surface 42 of tray 20 and wall 126 of tray 20 and further covered by wall 32 of lip 30. As depicted in FIG. 8, wall 32 covers recess 14 a distance 128 before recess 14 is exposed to opening 16 through mouth 40. The portion of recess 14 shown in FIG. 8 may only be accessible through mouth 40 to interior of tray 20. Mouth 40 and opening 16 fluidically expose any elongated medical device 12 received by recess 14.

Figure 9:
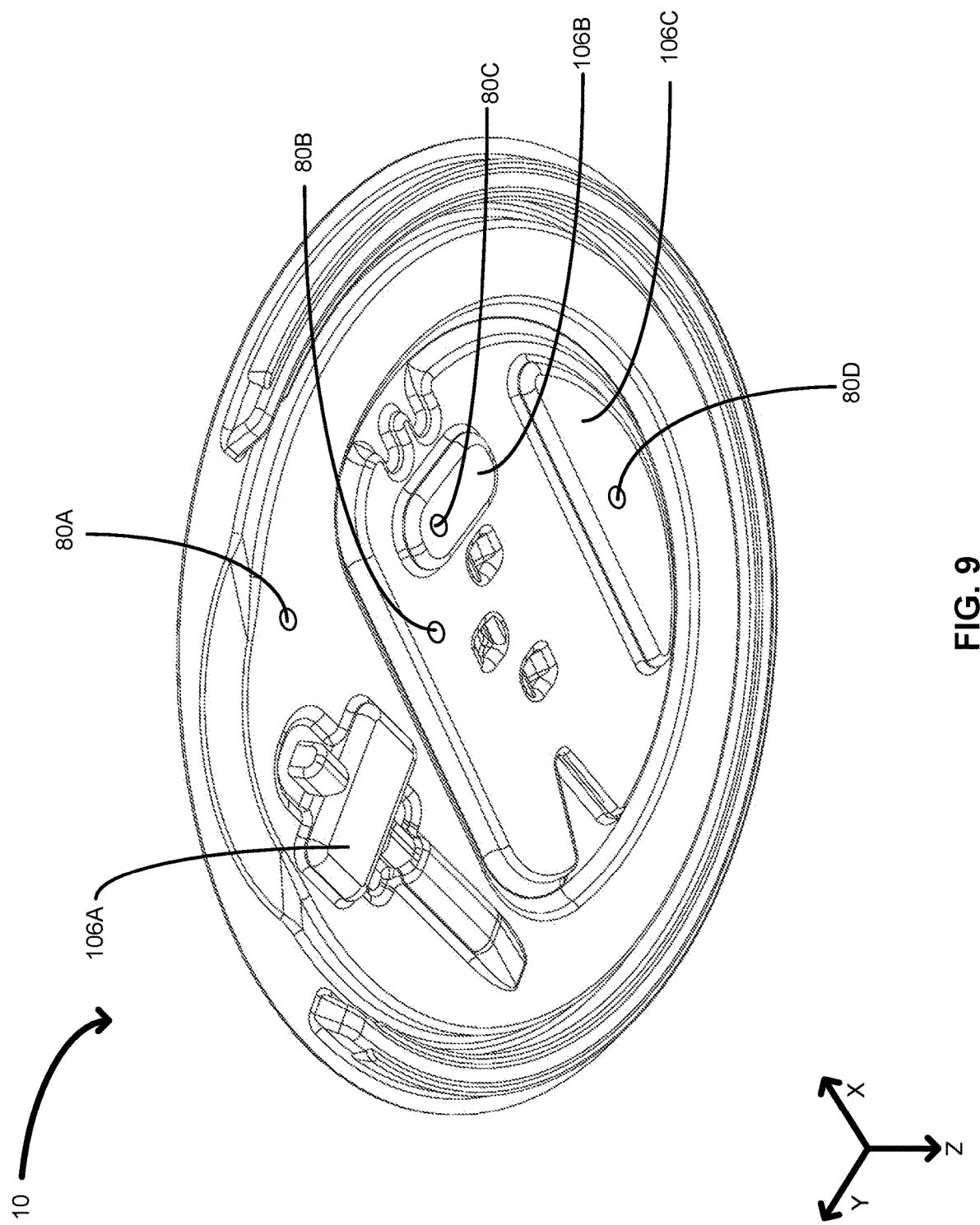
FIG. 9 depicts a perspective view of the bottom of the medical device package of FIG. 1.

FIG. 9 depicts a perspective view of the bottom of an example medical device package 10. FIG. 9 depicts drain holes 80 of tray 20. FIG. 9 also depicts bottom surfaces 106A-C (collectively "bottom surfaces 106") of tray 20 that comprise bottom surface 106 of FIG. 6B. Bottom surfaces 106 may be configured to provide a generally flat and stable surface on which medical device package 10 may rest when placed on a surface (e.g., a table or cabinet or shelf). In some examples, when medical device package 10 is arranged on a surface with opening 16 facing "up" such that it opening 16 and/or elongated medical device 12 is visible to a clinician, medical device package 10 is configured to contact the surface with bottom surface 106.

Figure 10:
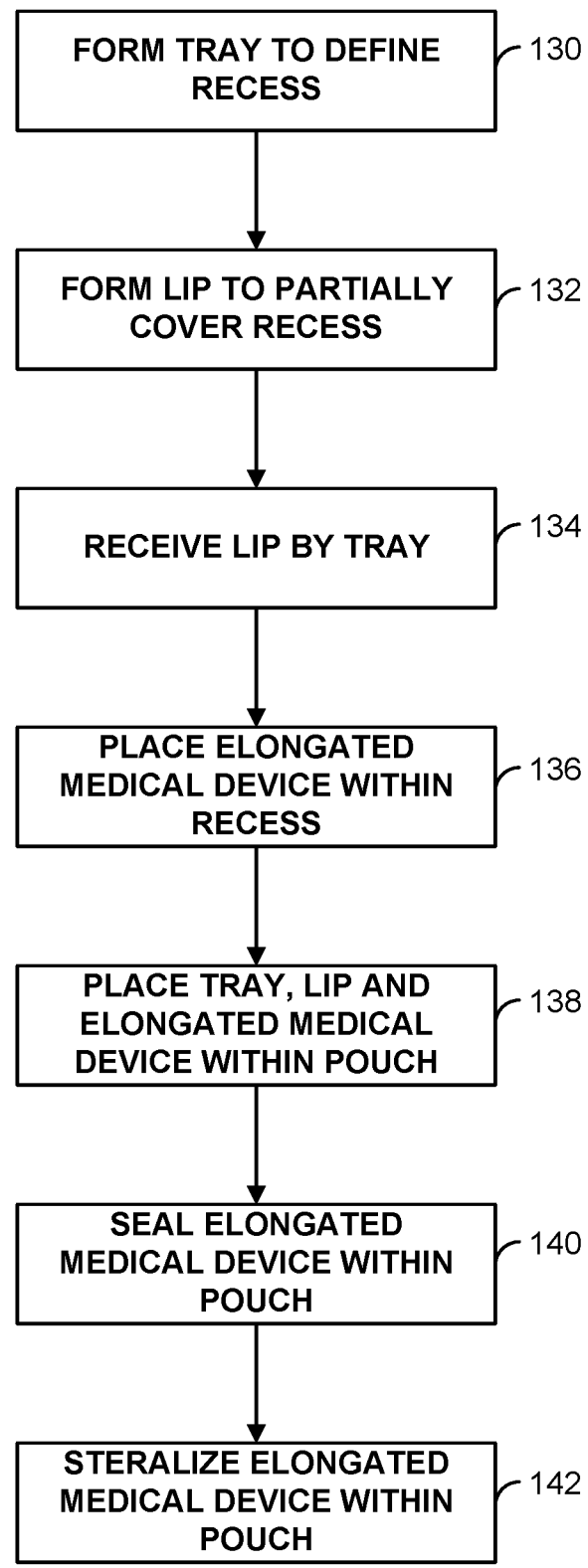
FIG. 10 is a flow diagram of an example method of forming the catheter of FIG. 1.

The medical device packages described herein can be formed using any suitable technique. FIG. 10 is a flow diagram of an example method of forming medical device package 10. In accordance with the technique shown in FIG. 10, tray 20 may be formed to define recess 14 (130). In some examples, tray 20 may be formed as a unitary, seamless body.

As discussed above, tray 20 defines a recess 14. For example, as shown in FIG. 1, recess 14 may have a circular planform. Tray 20 may be configured to receive lip 30. For example, as depicted in FIG. 2, tray 20 may be configured to define channel 52 in which groove 34 of lip may be received. Tray 20 may be formed from any suitable material. For example, tray 20 may be formed from PETG or Tritan.

Lip 30 may be formed (132) such that lip 30 is configured to be received by tray 20 as depicted in FIG. 1. Lip 30 may be configured to cover a portion 128 of recess 14 as depicted in FIG. 8. Lip 30 may be received by received by tray 20 (134). As depicted in FIG. 8, tray 20 and lip 30 may define mouth 40 to recess 14. Lip 30 and tray 20 may be formed such that, when tray 20 receives lip 30, mouth 40 is configured to facilitate the removal of elongated medical device 12 as depicted in FIGS. 3 and 4. Mouth 40 may be configured to facilitate the removal of elongated medical device 12 while elongated medical device 12 is in coiled state 50 as depicted in FIG. 2.

Lip 20 and tray 30 define opening 16 as depicted in in FIG. 1. Opening 16 is configured to expose elongated medical device 12 that is received within recess 14. Elongated device may be placed in recess 14 or removed from recess 14 through opening 16.

Elongated medical device 12 may be placed within recess 14 of tray 20 (136). Elongated medical device 12 may be in coiled state 50 within recess 14. As discussed above, elongated medical device 12 may be fluidically exposed through opening 16 when tray 20 and lip 30 are at least partially submerged within a hydrating fluid. Upon being at least partially submerged, the entirety of elongated medical device 12 may be exposed to and therein contacted by the hydrating fluid.

As depicted in FIG. 6A, tray 20 and/or lip 30 may be formed to define a profile that mates in interlocking fashion with other trays and lips that have been formed substantially similarly to tray 20 and lip 30. Forming trays 20 and lips 30 to define interlocking profiles may facilitate the stacking and interlocking of a plurality of (e.g., a dozen) medical device packages 10 to be placed in a hydrating container filled with hydrating fluid simultaneously with little concern for the stack of medical device packages 10 becoming unbalanced or otherwise un-mated. Further, trays 20 and lips 30 may be formed such that each elongated medical device 12 may maintain fluidic exposure even while a respective medical device package 10 is interlocked with a plurality of medical device packages 10.

Tray 20, lip 30, and elongated medical device 12 within recess 14 may be received by pouch 82 as depicted in FIG. 5 (138). In some examples, tray 20, lip 30, and elongated medical device 12 may be sealed within pouch 82 (140). Elongated medical device 12 may be sterilized (142). Tray 20 may be formed to facilitate elongated medical device 12 being sterilized within recess 14 of tray 20. Further, tray 20 and pouch 82 may be formed to facilitate elongated medical device 12 being sterilized when elongated medical device 12 is received within recess 14 of tray 20 within pouch 82. In some examples, elongated medical device 12 may be sterilized when elongated medical device 12 is received within recess 14 of tray 20 within pouch 82 even when pouch 82 has been sealed.

Various examples of the disclosure have been described. Any combination of the described systems, operations, or functions is contemplated. These and other examples are within the scope of the following claims.

What is claimed is:

1. A medical device package comprising:
a tray defining a recess configured to receive an elongated medical device in a coiled state;
a lip configured to cover at least a portion of the recess, the lip and tray defining a mouth to the recess;
the elongated medical device within the recess; and
a pouch,
wherein the tray and lip define an opening configured to expose the elongated medical device when the elongated medical device is received in the recess, the mouth being configured to facilitate removal of the elongated medical device from the recess through the opening while the elongated medical device is in the coiled state, and wherein the tray, the lip, and the elongated medical device are within the pouch.

2. The medical device package of claim 1, wherein the tray defines a generally flat major surface, wherein the elongated medical device rests on the major surface when the elongated medical device is received in the recess.

3. The medical device package of claim 2, wherein the major surface is generally continuous within the recess.

4. The medical device package of claim 1, wherein the recess extends around an entirety of a perimeter of the tray.

5. The medical device package of claim 1, wherein the opening fluidically exposes an entirety of the elongated medical device when the elongated medical device is received by the recess.

6. The medical device package of claim 1, wherein the recess is configured such that the elongated medical device contacts a surface of the tray that runs along a perimeter of the tray and is generally opposite the mouth when the recess receives the elongated medical device in the coiled state.

7. The medical device package of claim 1, wherein the lip recedes to a perimeter of the tray.

8. The medical device package of claim 1, wherein the lip is flexible such that the lip is configured to flex in response to a force of the elongated medical device being pulled laterally from the medical device package in the coiled state.

9. The medical device package of claim 1, wherein the tray defines a profile configured to mate with another medical device package.

10. The medical device package of claim 1, wherein the tray defines a drain hole configured to drain fluid from the recess.

11. The medical device package of claim 1, wherein the coiled state includes a plurality of loops of the elongated medical device.

12. The medical device package of claim 1, wherein the tray defines a generally circular planform through the recess.

13. The medical device package of claim 1, wherein the tray defines a generally ovaloid planform through the recess.

14. The medical device package of claim 1, the tray further comprising one or more strengthening ribs.

15. The medical device package of claim 14, wherein the one or more strengthening ribs are located on a surface opposite the opening.

16. The medical device package of claim 1, wherein the recess as defined by the tray is continuous with a circular planform.

17. The medical device package of claim 1, wherein the tray includes a retention member configured to retain a medical component that is structurally separate from the elongated medical device.

18. A medical device package comprising:
a tray defining a recess configured to receive an elongated medical device in a coiled state;
the elongated medical device within the recess in the coiled state;
a lip configured to cover a portion of the recess and retain the elongated medical device within the portion of the recess, wherein the lip and tray define a mouth configured to provide access to the portion of the recess; and
a pouch;
wherein the tray and lip define an opening configured to expose the elongated medical device when the elongated medical device is received in the recess, the mouth being configured to facilitate removal of the elongated medical device in a lateral direction from the recess through the opening while the elongated medical device is in the coiled state, and wherein the tray, the elongated medical device, and the lip are within the pouch.

19. The medical device package of claim 18, wherein the elongated medical device is retained by an inner edge of the lip that has a radius that is greater than a radius of an outer edge of the lip minus a linear distance between the outer edge and the inner edge such that the lip extends away from the tray as the lip radially extends toward a center of the tray.

20. The medical device package of claim 18, wherein the tray defines an indentation configured to retain at least a portion of the elongated medical device.

21. The medical device package of claim 20, wherein the indentation is configured to retain the portion of the elongated medical device at a location physically separate from the recess.

22. The medical device package of claim 20, wherein the indentation is retaining at least one of a stent location or a hub of the elongated medical device.

23. A medical device package comprising:
   a tray defining a major surface and a first wall that extends out from the major surface along a perimeter of the major surface, the major surface and the first wall defining a recess configured to receive an elongated medical device in a coiled state;
   a lip connected to the first wall and extending around a portion of the perimeter of the major surface, the lip being configured to cover a part of the recess, and the lip and the major surface of the tray defining a mouth to the recess;
   the elongated medical device within the recess; and
   a pouch;
   wherein the lip and tray define an opening configured to expose the recess, the mouth being configured to facilitate removal of the elongated medical device from the part of the recess while the elongated medical device is in the coiled state, wherein the medical device package is configured to facilitate the removal of the elongated medical device in a radial direction away from the portion of the perimeter, and wherein the tray, the lip, and the elongated medical device are within the pouch.

24. The medical device package of claim 23, wherein an inner edge of the lip has a radius that is greater than a radius of an outer edge of the lip minus a linear distance between the outer edge and the inner edge such that the lip extends away from the tray as the lip radially extends toward a center of the tray.

25. The medical device package of claim 1, wherein an inner edge of the lip has a radius that is greater than a radius of an outer edge of the lip minus a linear distance between the outer edge and the inner edge such that the lip extends away from the tray as the lip radially extends toward a center of the tray.

* * * * *